United States Patent [19]

Sagstetter

[11] Patent Number: 5,409,112

[45] Date of Patent: * Apr. 25, 1995

[54] NEEDLE DISPOSAL SYSTEM COMPRISED OF BLOOD COLLECTION HOLDER AND COMPANION BIOHAZARD RECEPTACLE

[75] Inventor: William E. Sagstetter, Denver, Colo.

[73] Assignee: Medical Safety Products, Inc., Englewood, Colo.

[*] Notice: The portion of the term of this patent subsequent to Feb. 11, 2009 has been disclaimed.

[21] Appl. No.: 156,083

[22] Filed: Nov. 22, 1993

Related U.S. Application Data

[63] Continuation of Ser. No. 708,900, May 31, 1991, Pat. No. 5,273,161.

[51] Int. Cl.$^6$ ............................................. A61M 5/32
[52] U.S. Cl. ................................... 206/366; 220/908
[58] Field of Search ................. 604/205, 413, 110; 128/763, 764, 770; 206/364, 366, 367, 368, 369, 370; 220/908

[56] References Cited

U.S. PATENT DOCUMENTS

| | | | |
|---|---|---|---|
| 5,067,223 | 11/1991 | Bruno | 206/366 X |
| 5,069,667 | 12/1991 | Freundlich et al. | 206/366 X |
| 5,086,922 | 2/1992 | Sagstettes et al. | 206/366 |
| 5,092,462 | 3/1992 | Sagstetter et al. | 206/366 |
| 5,273,161 | 12/1993 | Sagstetter | 206/366 |

Primary Examiner—Jacob K. Ackun
Attorney, Agent, or Firm—Dorr, Carson, Sloan & Birney

[57] ABSTRACT

A needle disposal system has a blood collection holder with an engaged blood collection needle and a companion biohazard receptacle for disposal of the needle after use. First, the blood collection needle engaged to the holder is irreversibly positively locked upon insertion into respective needle removal device of the biohazard receptacle, thereby preventing withdrawal of the needle from the biohazard receptacle. The needle is then unthreaded from the holder and disposed of inside the biohazard receptacle.

18 Claims, 6 Drawing Sheets

NEEDLE DISPOSAL SYSTEM COMPRISED OF BLOOD COLLECTION HOLDER AND COMPANION BIOHAZARD RECEPTACLE

RELATED APPLICATION

This application is a continuation of the Applicant's U.S. patent Application Ser. No. 07/708,900, filed on May 31, 1991, now U.S. Pat. No. 5,273,161.

BACKGROUND OF THE INVENTION

1. Field of the Invention

The present invention relates to a blood collection holder with an engaged blood collection needle and a companion biohazard receptacle for disposal of a needle and, more particularly to a blood collection system comprised of means in which a blood collection needle engaged to a holder is irreversibly positively locked when inserted into a needle removal device of a biohazard receptacle, thereby preventing withdrawal of the needle from the biohazard receptacle, following which the needle is unthreaded from the holder and disposed inside the receptacle.

2. Description of the Prior Art

To obtain a blood sample, blood is drawn into an evacuated blood collection tube through a double ended needle. The needle includes a hub, an anterior needle for tissue penetration into a blood vessel and a posterior needle having an exterior elastomeric valve. The posterior end of the needle is penetrably inserted within a holder having female threads for threadedly engaging the hub to retain the double ended needle positionally fixed with respect to the holder. A common example of this conventional holder is sold under the brand name VACUTAINER ®. The proximal end of the holder is open to receive an evacuated blood collection tube having a stopper for penetrably receiving the posterior needle. During venipuncture, blood will flow through the anterior needle and the posterior needle into the collection tube. When the collection tube is removed, the elastomeric valve recovers the posterior needle to prevent spontaneous blood flow from the needle. Upon completion of the venipuncture procedure, the anterior needle is withdrawn from the patient's vein. While the holder is often reused, the double ended needle must be safely removed from the holder, without causing needle stick and contact with the contaminated needle. Typically, a conventional biohazard receptacle for needles is provided with a lid having various shaped slots to engage the needle hub. To dispose of a used needle, the phlebotomist must carefully place the exposed needle hub into the slot, grip and rotate the holder to unthread the needle and cause the disengaged needle to drop completely through the slot into the underlying container. A danger arises after the needle is disengaged from a holder if the hub remains engaged in the slot, causing upstanding exposure of the posterior needle. The user must manually disengage the hub from the slot to permit the needle to drop into the receptacle. In addition, when the hub is engaged in the slot, there is no positive locking mechanism to irreversibly grip the needle hut and prevent the needle from moving outwardly from the slot. Thus a user may engage the needle hub into a slot, incompletely unthread the needle from the holder, lift the holder with the partially attached needle away from the biohazard container which will cause dangerous exposure to a used needle. Aside from hub engaging slots, other devices have been developed including the use of fixed and movable jaws to engage the needle hub. These devices exhibit a positive locking means for retaining the needle in the needle removal mechanism. These positive locking means are reversible to allow release of a disengaged needle from the needle removal mechanism. Thus, the user can be endangered if the positive locking means is prematurely released, allowing exteriorization of the needle from the biohazard receptacle. Mechanized devices for unthreading a double ended needle are also known but these mechanisms also lack irreversible positive locking means which can potentially cause the needle to exteriorize outside of the biohazard devices.

A recently available reusable safety blood collection holder (i.e. ACCI-GUARD ® HOLDER which is described in co-pending patent application: BLOOD COLLECTION TUBE HOLDER, Ser. No. 430,311), includes an insert for engaging the double ended needle. The insert is translatable within the holder to fully enclose and shield both the anterior and posterior needles of the double ended needle. The holder includes an anterior collar for shielding the pointed end of the anterior needle upon posterior retraction of the insert within the holder. Known syringe and needle removal mechanisms are not well suited for receiving and disposing needles from such devices since the hub of the double ended needle is shielded by the anterior collar and is not accessible for gripping by the opposed edges of a slot, jaws or the like.

In co-pending applications, DISPOSAL FOR NEEDLES AND SYRINGES (Ser. No. 536,708) and DISPOSAL FOR DISENGAGING AND RECEIVING NEEDLES (Ser. No. 536,378), biohazard receptacles with needle removal mechanisms are described. These two co-pending patent applications describe needle removal devices which are compatible with currently available holders of the VACUTAINER ® and ACCI-GUARD ® types, creating a safety blood collection system. However this safety blood collection system has no structural means to ensure that a double ended blood collection needle is irreversibly positively locked when inserted into the needle removal devices, which would prevent withdrawal of the needle from the biohazard receptacle.

SUMMARY OF THE INVENTION

Holders of the VACUTAINER ® type and ACCI-GUARD ® types have anterior bosses with female threads into which a double ended needle is threadedly engaged. The diameters of the anterior bosses of both types of holders are typically the same or greater than the diameter of a double ended needle hub. Modified blood collection holders described in this patent application are designed so that the diameters of the anterior bosses are smaller in diameter as compared to the diameter of a double ended needle hub. Henceforth, when a double ended needle attached to these modified holders is inserted into respective needle removal devices described in the aforementioned patent applications, a leaf spring will be able to access and bias against the posterior surface of the needle hub. This will create an irreversible positive lock of a blood collection needle that has been inserted into a biohazard receptacle, thereby preventing withdrawal of the needle from the biohazard receptacle.

It is therefore a primary object of the present invention to provide a blood collection system which will permit irreversible positive gripping of a blood collection needle inside a needle removal device of a biohazard receptacle, thereby preventing withdrawal of the needle from the biohazard receptacle.

Another object of the present invention is to provide an irreversible positive locking mechanism for a needle inserted into a needle removal device, thereby preventing withdrawal of the needle from the biohazard receptacle, which needle removal device is comprised of a post for engaging a rib of the needle hub allowing unthreading of the needle from a holder, and a leaf spring for actively urging the disengaged needle into the interior of the biohazard receptacle by biasing on the posterior surface of the needle hub.

Yet another object of the present invention is to provide a blood collection system which will permit a single hand technique to irreversibly positively lock a blood collection needle inside an accessible biohazard receptacle, thereby preventing withdrawal of the needle from the biohazard receptacle, following which the needle will disengage from the holder and fall freely into the interior of a biohazard receptacle.

A still further object of the invention is to provide a system for safe blood collection when a biohazard container is not readily accessible. This system allows single hand point of use protection of a used needle within a translatable holder, transporting the holder to a biohazard container, and single handedly inserting the holder-needle combination into a biohazard receptacle causing irreversible positive locking of the needle, thereby preventing withdrawal of the needle from the biohazard receptacle. Following this step, the needle will disengage from the holder and then fall freely inside the biohazard receptacle.

These and other objects of the present invention will become apparent to those skilled in the art as the description thereof proceeds.

BRIEF DESCRIPTION OF THE DRAWINGS

The present invention will be described with greater clarity and specificity with reference to the following drawings, in which.

DESCRIPTION OF THE PREFERRED EMBODIMENT

The merit of the invention described in this application will become apparent after a review of the prior art described in the following co-pending applications: BLOOD COLLECTION TUBE HOLDER, Ser. No. 430,311; DISPOSAL FOR NEEDLES AND SYRINGES, Ser. No. 536,708; DISPOSAL FOR DISENGAGING AND RECEIVING NEEDLES, Ser. No. 536,378.

Figure 1:
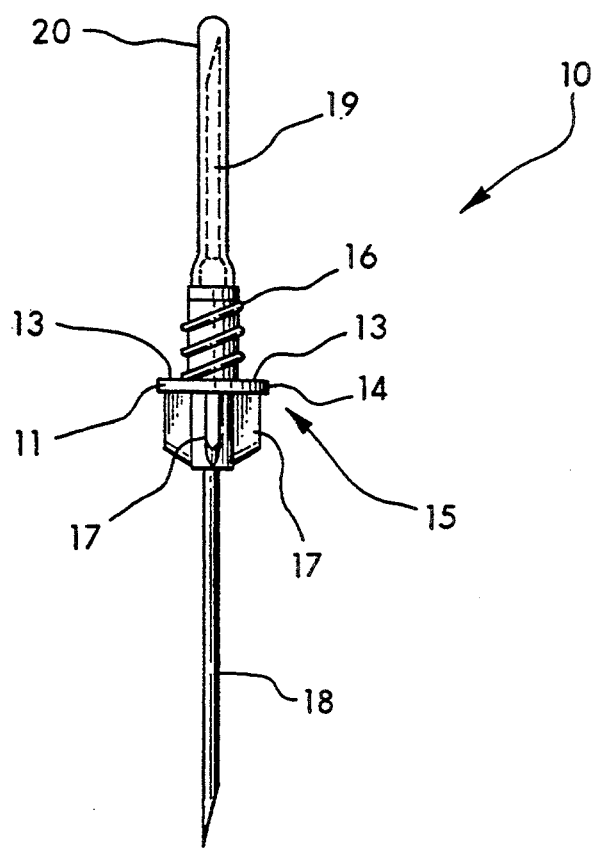
FIG. 1 is an isometric view of a double ended blood collection needle.
Figure 2:
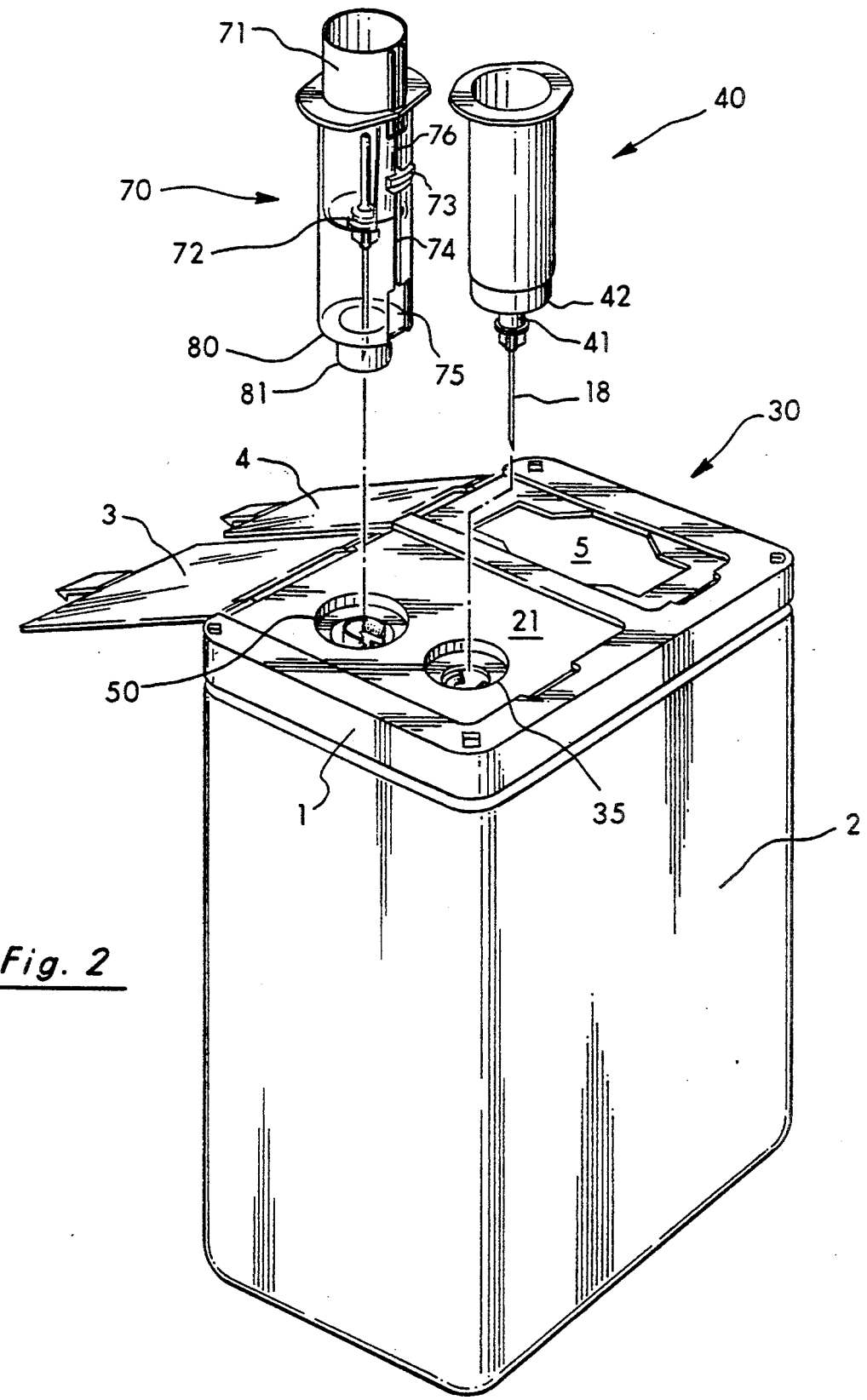
FIG. 2 is an isometric view of a biohazard receptacle with needle removal devices for engaging the hubs of double ended needles threadedly engaged with two types of modified blood collection holders.
Figure 3:
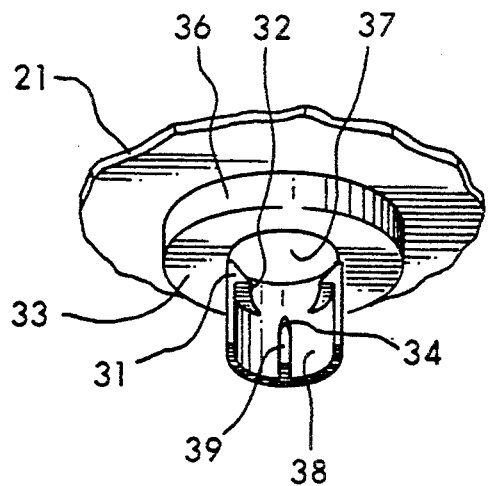
FIG. 3 is an isometric view of needle removal device in FIG. 2 for one type of modified blood collection holder.
Figure 4:
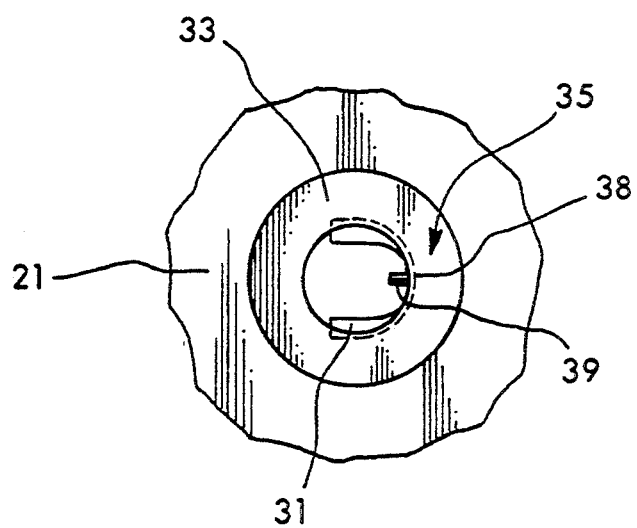
FIG. 4 is a top view of needle removal device illustrated in FIG. 3.
Figure 5:
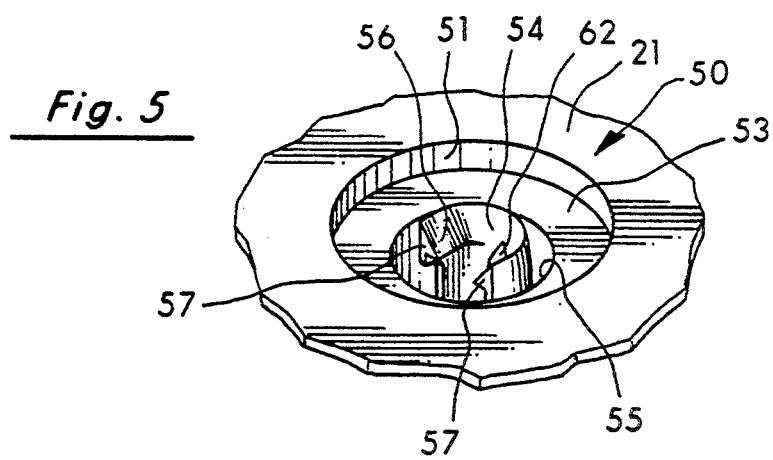
FIG. 5 is an isometric view of another needle removal device in FIG. 2 for a modified holder with a translating insert.
Figure 6:
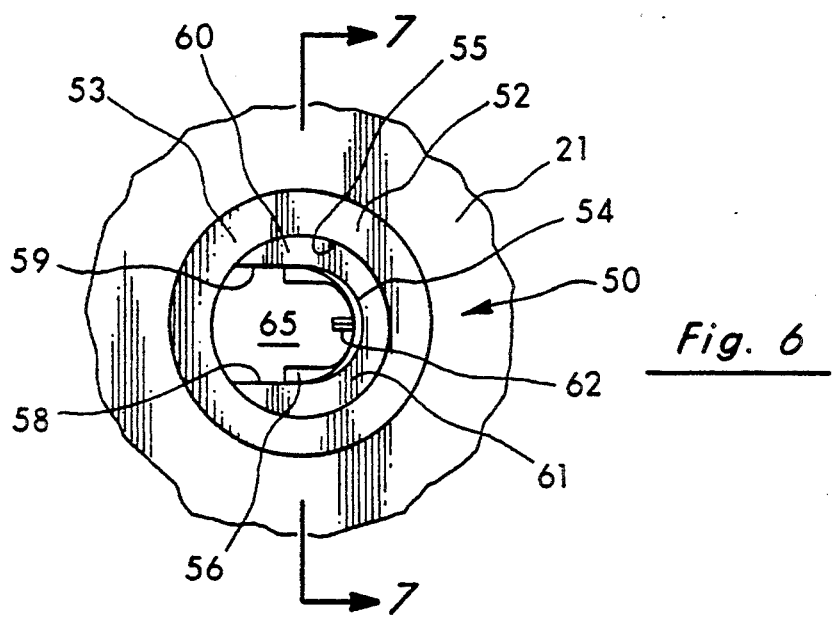
FIG. 6 is a partial top view of needle removal device illustrated in FIG. 5.
Figure 7:
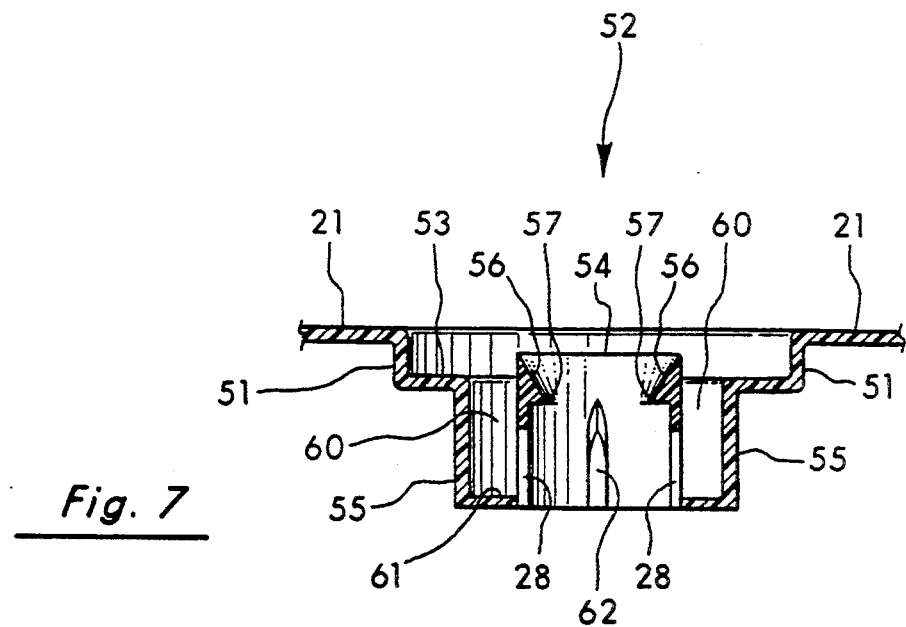
FIG. 7 is a cross sectional view taken along lines 7—7 as shown in FIG. 6.
Figures 8A, 8B:
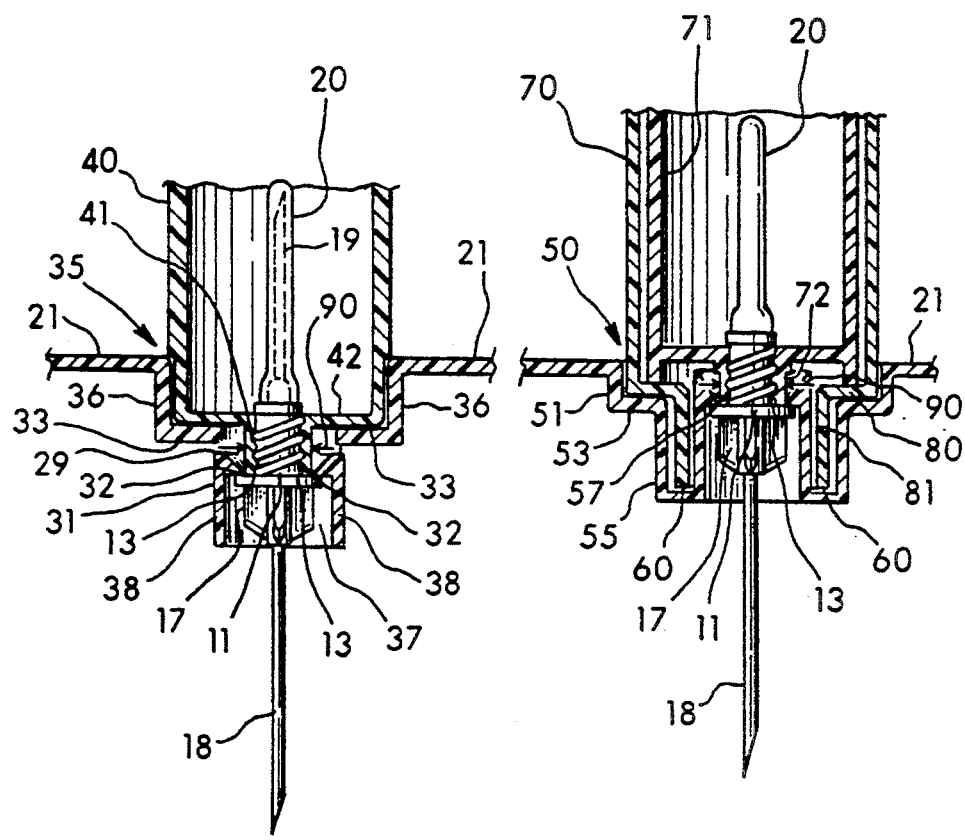
FIG. 8 is a partial sectional view illustrating the relationships between needle removal devices engaging needle hubs which are attached to respective modified types of blood collection holders.

FIG. 1 illustrates a conventional double ended needle 10 with a band 11 disposed about the hub 15 intermediate the threaded segment 16 and the ribbed segment 17. The double ended needle 10 is comprised of an anterior needle 18, a posterior needle 19 and an elastomeric valve 20 which covers the posterior needle 19. FIG. 2 illustrates a biohazard receptacle 30 comprised of a top 1, base receptacle 2 to which the top 1 is permanently attached, aperture 5 for disposal of large medical waste, hinged lids 3,4 to lock over apertured needle removal devices 35,50 and aperture 5. Recessed needle removal devices 35,50 are used respectively with a modified blood collection holder 40 of the VACUTAINER® type and a modified blood collection holder 70 with a translatable insert of the ACCI-GUARD® type. A double ended needle 10 is threadedly engaged to the anterior boss 41 of the holder 40. FIGS. 3 and 4 illustrate the needle removal device 35 for holder 40. A cylindrical wall 36 depends from top surface 21 to define a cylindrical recess 35 to receive and support cylindrical anterior end 42 of the holder 40. An annular base 33 extends radially inwardly from the cylindrical wall 36 to support the holder 40. A semi-cylindrical skirt 38 depends from the annular base 33 proximate aperture 37 formed centrally of the annular base 33. The interior diameter defined by cylindrical wall 36 is approximately equivalent to that of anterior end 42 of the blood collection holder 40. The interior diameter of semi-cylindrical skirt 38 is approximately that defined by hub 15 of double ended needle 10. A longitudinally oriented post 39 extends radially inwardly from semi-cylindrical skirt 38. The extent of radial inward extension of post is sufficient to interferingly engage with one of the ribs 17 on hub 15 upon insertion of anterior end 42 of holder 40 within the recess 35. The post 39 will interferingly engage a rib 17 of the hub 15 to prevent rotation of the hub 15 commensurate with counterclockwise rotation of the holder, thereby causing threaded disengagement of the hub 15 from the holder 40. To encourage drop of double ended needle into receptacle 30 upon threaded disengagement with the holder, the end 34 of the post 39 may be canted inwardly downwardly as a ramp to encourage downward sliding movement of the double ended needle into the interior of receptacle. Due to manufacturing tolerance or for other reasons, disengagement between the double ended needle 10 and holder 40 may require application of a force more positive than that of gravity. To ensure disengagement after unthreading, one or more leaf spring(s) 31 is formed in top of semi-cylindrical skirt 38 by a horizontal separation 29 (FIG. 8A) between base 33 and top of free end of semi-cylindrical wall 38. The interior upper end of leaf spring includes an inwardly directed lip 32. When the anterior needle 18 and hub 15 are inserted into the recess 35, the leaf spring 31 moves radially outwardly to accommodate transport of the hub 15 past the leaf spring lip 32. Until the needle begins to unthread from the holder, the lip 32 of leaf spring 31 may bias against the exterior surface of the needle hub 15, the exterior surface 14 of the needle band 11 or the anterior boss 41 of the holder 40. Once the rib hub 17 engages the post 39 and the holder 40 is rotated counterclockwise, the needle begins to unthread from the anterior boss 41 of the holder 40. The lip 32 of the leaf spring will then bias radially inwardly until it engages the posterior surface 13 of the needle band 11, and interfere with upward withdrawal of the hub upon upward movement of the holder from the recess.

A more complex modified holder (ACCI-GUARD®) 70, shown in FIG. 2, has been developed to provide point of use protection from a used needle. This holder 70 has a translatable insert 71 with a boss 72 disposed at the anterior end for threadedly engaging a hub 15 of a double ended needle 10. A spring loaded tab 73 integrally attached to the insert 71 extends through the holder for penetrable engagement with and translation along a slot 74 formed longitudinally in the holder 70. The slot 74 includes an anterior laterally expanded segment 75 and a posterior laterally expanded segment 76 for receiving the tab 73 to lockingly retain insert 71 in the anterior 75 or posterior 76 positions. The length of the insert 71 is sufficient to fully enclose posterior needle 19 to prevent contact with that end of the needle. Upon translation of insert 71 to its posterior position 76, anterior needle 18 is enclosed within the anterior 80 portion of holder 70. Anterior end of holder includes a collar 81 for accommodating penetration therethrough of anterior needle. Upon retraction of insert 71 to its posterior position 76, the pointed end of the anterior needle 18 may be located within the confines of the anterior collar 81. To accommodate disengagement of double ended needle 10 from holder 70 on completion of venipuncture, biohazard receptacle 30 with recessed needle removal device 50 may be used (FIGS. 2, 5–8). A cylindrical wall 51 extends downwardly from top surface 21 and defines an aperture 52. A base 53 extends radially inwardly from a part of the lower end of the cylindrical wall 51 to support cylindrical anterior end 80 of holder 70. A cylindrical skirt 55 depends from the base 53. A three-quarter annular floor 61 extends radially inwardly from cylindrical skirt 55 for supporting an upwardly extending semi-cylindrical flange 54. An aperture 65 communicating with the interior of the receptacle is defined by the walls of the flange 54. The flange 54 is radially inwardly displaced from the interior surface of cylindrical skirt 55 to form a slot 60 with bottom defined by floor 61. The slot 60 has a radial width commensurate with the radial width of collar 81 of holder 70. The bottom of the semi cylindrical flange 56 has horizontal separation(s) 28 between floor 61 and free ends of flange 54 to form leaf spring(s) 56. The upper end of the leaf spring(s) 56 includes a radially inwardly oriented lip 57. The top of the lip 57 may be canted downwardly inwardly to define a ramp. The floor 61 may be terminated by edges 58,59 which extend tangentially from flange 54 to cylindrical skirt 55. A post 62 extends radially inwardly from semi cylindrical flange 54 at its approximate mid point. The upper end of the post may be canted downwardly to define a ramp. In operation, collar 81 of holder 70 is inserted within slot 60 defined by cylindrical skirt 55 and semi cylindrical flange 54. Support of holder may be provided by holder resting on surface 53 and by collar resting upon floor 61 or either one. After placement of collar within slot 60, tab 73 of holder 70 is translated to anterior expanded lateral segment 75, thereby positioning anterior needle 18 into interior of receptacle 30. A rib 17 of the hub 15 will interferingly engage the post 62. The inward extension of post 62 is sufficient to extend adjacent the body of hub and intermediate ribs 17 of the hub to interferingly engage a hub rib 17 during rotation of the holder about its longitudinal axis. Thus, counterclockwise rotation of the holder 70 will result in unthreading and disengagement of the double ended needle 10 from the holder. Upon withdrawal of the holder 70 the needle 10 will drop through the aperture 65 into the receptacle 30. Until the needle begins to unthread from the holder, the lip 57 of leaf spring 56 may bias against the the exterior surface of the needle hub 15, the exterior surface 14 of the needle band 11 or the anterior boss 72 of the holder 70. Once the rib 17 of hub engages the post 62 and the holder 70 is rotated, the needle begins to unthread from the anterior boss 72 of the holder 70. The lip 57 of the leaf spring 56 will then bias radially inwardly until it engages the posterior surface 13 of the needle band 11, interfering with upward withdrawal of the needle 10 upon upward movement of the holder 70 from the recess 50 and at the same time actively urge the disengaged needle into the interior of the receptacle 30. The ramp of the post will encourage downward sliding of the disengaged needle into the receptacle.

Operation of holders of the VACUTAINER® and ACCI-GUARD® (i.e. without modification as described in the present patent) in their respective needle removal devices 35,50 will occasionally allow the needle to be withdrawn from the biohazard receptacle. This occurs because the respective leaf spring lip 31,57 will bias radially inwardly on either the needle hub 15, the exterior outer surface 14 of the needle band or the anterior boss of the respective holder. When that occurs, the leaf spring lip 31,57 will not be able to create an irreversible positive lock by positioning itself onto the posterior surface 13 of the needle band 11. As a result, a needle engaged to either unmodified holder will not be irreversibly positively locked by the leaf spring bias within the needle removal devices 35,50. Henceforth, in this circumstance there is a possibility that the used needle could exteriorize outwardly from the biohazard container. This problem has necessitated developing a structural means to ensure that a needle will be irreversibly positively locked when it is inserted into either needle removal device 35,50. In order to accomplish this goal, the lip 32,57 of the leaf spring must be able to irreversibly grip the needle such as by biasing against the posterior surface 13 of the needle band 11. FIG. 8 illustrates the preferred embodiment of this invention which accomplishes this goal by reducing the diameter 90 of the anterior boss 41,72 of the respective modified holders 40,70 in relation to the diameter of the needle band 11. It is important to note that unmodified holders of the VACUTAINER® and ACCI-GUARD® types are typically manufactured with the diameter of the anterior boss being equivalent to or greater than the diameter of the needle band 11 of a double ended needle. Henceforth, by modifying these holders the smaller diameter of the anterior boss 41,72 permits the respective leaf spring lip 32,57 to access and bias against the posterior surface 13 of the needle band 11, thereby gripping the needle with an irreversible positive locking mechanism that precludes movement of the needle outwardly from the biohazard container.

When the leaf spring lip 32,57 accesses the posterior surface 13 of the needle band, an audible click will indicate that the needle is irreversibly positively locked within the biohazard container. Once the needle is irreversibly locked, it will become disengaged from the holder during counterclockwise rotation of the holder in relation to the biohazard container, following which it will be actively urged into the interior of the biohazard container by the spring action of the leaf spring(s) 31,56.

Figure 9:
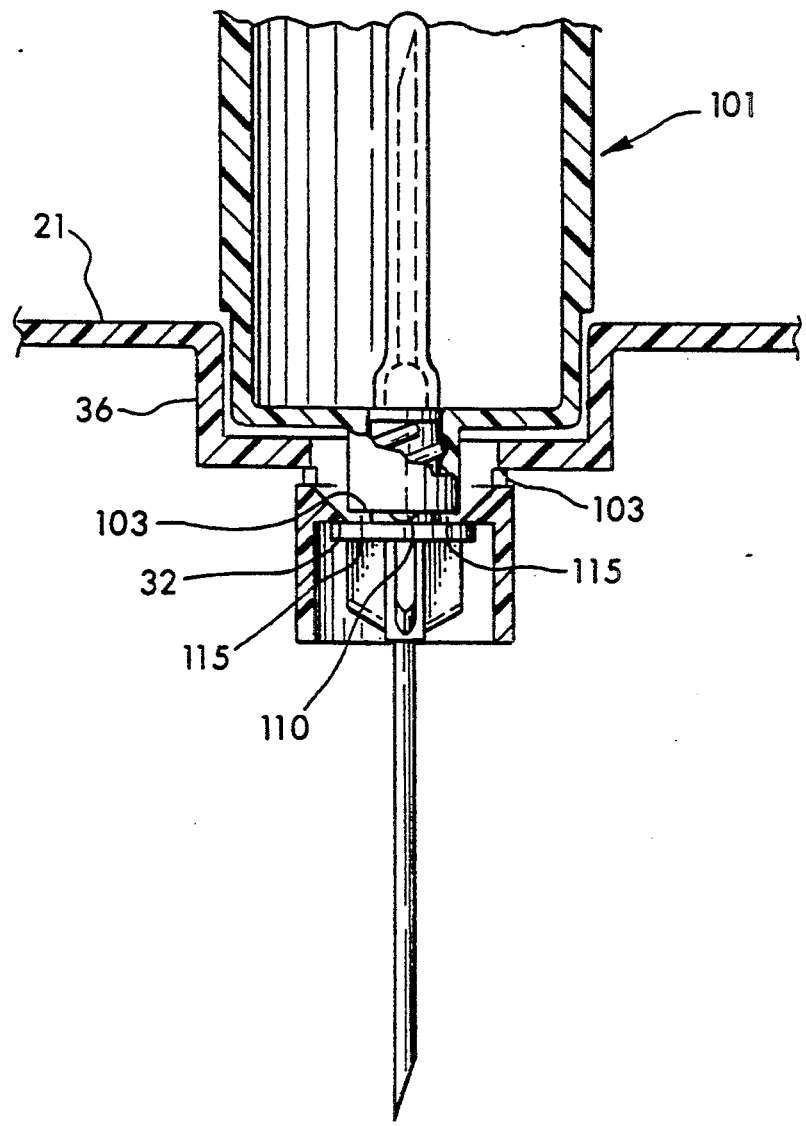
FIG. 9 is a partial sectional view illustrating the relationship between a needle removal device engaging a needle hub which is attached to a variant modification of a VACUTAINER® type blood collection holder with spacer interference.

FIG. 9 illustrates a second embodiment of a variant modification of a VACUTAINER ® type holder 101. This embodiment also permits access and bias of the leaf spring lip 32 onto the posterior surface 13 of the needle band 11, thereby producing an irreversible positive lock of the needle within the biohazard receptacle. In the second embodiment, an interference spacer 110, such as one or more beads located on the anterior end of boss 103 of variant modified holder 101, will create a space 115 between the posterior surface 13 of the seated double ended needle 10 and the anterior and of boss 103. This space 115 permits access and bias of the leaf spring lip 32 onto the posterior surface 13 of the needle band. The spacer interference design is also adaptable for an ACCI-GUARD ® type of holder with a translatable insert. It is also possible to gain access to the posterior surface 13 of the needle tand 11 by manufacturing a double ended needle with a needle band 11 that is larger in diameter than the diameter of the anterior boss of unmodified holders of the Vacutainer ® and ACCI-GUARD ® types. The relatively smaller diameter of the anterior boss of these holders in relation to the larger diameter of the needle band will permit access and bias of the leaf spring lip 32,57 onto the posterior surface 13 of the needle band.

The addition of a structural element to permit irreversible positive locking of a needle within a needle removal device, which prevents withdrawal of the needle from the biohazard receptacle, adds immeasurable safety to the user. After blood collection, if a biohazard receptacle is accessible the user single handely can insert either modified holder 40,70 with engaged needle into the respective recessed needle removal devices 35,50 of the biohazard receptacle 30. When the holder and needle are seated properly into one of the needle removal devices 35,50, a click will be audible to the user indicating that the needle is irreversibly positively locked within the receptacle. In fact, the user can gently attempt to move the holder 40,70 outwardly from the receptacle and the irreversible positive lock retains the holder to the biohazard receptacle as long as the needle remains engaged to the holder. This maneuver will verify to the user that the needle is irreversibly positively locked within the receptacle. A counterclockwise twist of the holder in relation to the biohazard receptacle will unthread the needle which is then actively urged into the interior of the receptacle by the bias of the leaf spring. If a biohazard receptacle is not readily accessible, structure of holder 70 will permit point of use retraction of the anterior needle 18 within the holder 70 by translating tab 73 with insert 71 from the anterior position 75 to the posterior position 76. The user then transports the holder 70 to a biohazard receptacle 30, properly seats holder 70 into needle removal device 50, moves tab 73 to anterior position 75 to exteriorize needle into interior of receptacle, allows needle hub to become irreversibly positively locked within receptacle as indicated by audible click and inability to withdraw holder from receptacle, and then twists holder counterclockwise in relation to receptacle to unthread the needle which is then forcibly urged into the interior of the receptacle. Both blood collection methods provide safe protected removal of a used needle and offer alternatives to users in the medical profession.

Single ended needles attached to hypodermic syringes also have ribbed hubs. Accordingly, the first and second embodiments of this invention can be applied to syringes to develop a disposal system which will permit irreversible positive locking of a single ended needle within a biohazard receptacle.

While the principles of the invention have now been made clean in an illustrative embodiment, there will be immediately obvious to those skilled in the art many modifications of structure, arrangement, proportions, elements, materials and components used in the practice of the invention which are particularly adapted for specific environments and operating requirements without departing from those principles.

We claim:

1. A system for disposing of a double ended needle comprising:
 a double ended needle having an anterior end and a posterior end;
 a needle hub disposed on said double ended needle between said anterior end and said posterior end having:
  (a) a posterior threaded segment;
  (b) a segment having an enlarged diameter, and
  (c) an anterior ribbed segment; a blood collection holder having a boss for engaging said threaded segment of said needle hub; and
 a biohazard receptacle having:
  (a) an interior for storing said needle following disengagement from said holder;
  (b) an aperture for receiving the anterior end of said needle into said interior of said biohazard receptacle;
  (c) means for engaging said ribbed segment of said needle hub in said aperture for preventing rotation of said needle as said holder is rotated, thereby disengaging said needle from said holder; and
  (d) locking means for engaging said enlarged segment of said hub to prevent withdrawal of said needle from said aperture of said biohazard receptacle while said holder is rotated to disengage said needle from said holder and for urging the disengaged needle into said interior of said biohazard receptacle.

2. The system of claim 1 wherein said segment of said needle hub having an enlarged diameter comprises a posterior surface and said locking means comprises a leaf spring with a tip for engaging said posterior surface of said segment of said needle hub having an enlarged diameter.

3. The system of claim 1, wherein said segment of said needle hub having an enlarged diameter comprises a posterior surface and said biohazard receptacle further comprises a semi-cylindrical skirt within said aperture for contacting said needle hub, said semi-cylindrical skirt having a leaf spring formed as an inwardly directed lip on said semi-cylindrical skirt for engaging said posterior surface of said hub.

4. The system of claim 1, wherein said means for preventing rotation of said needle is comprised of a post disposed within said aperture for engaging said ribbed segment of said hub.

5. The system of claim 1, wherein said locking means produces an audible click when said locking means engages said enlarged segment of said hub.

6. A system for disposing of a double ended needle comprising:
- a double ended needle having an anterior end and a posterior end;
- a needle hub disposed on said double ended needle between said anterior end and said posterior end having:
  - (a) a posterior threaded segment;
  - (b) a horizontal band having an enlarged diameter and a posterior surface; and
  - (c) an anterior ribbed segment;
- a blood collection holder having an anterior collar and a translatable insert with a boss for engaging said threaded segment of said hub, said boss having a diameter that is smaller than the diameter of said horizontal band of said hub; and
- a biohazard receptacle having:
  - (a) an interior for storing said needle following disengagement from said holder,
  - (b) an aperture for receiving said collar of said holder and said anterior end of said needle into said interior of said biohazard receptacle;
  - (c) means for engaging said ribbed segment of said needle hub in said aperture for preventing rotation of said needle as said holder is rotated, thereby disengaging said needle from said holder, and
  - (d) locking means for engaging said posterior surface of said horizontal band of said hub to prevent withdrawal of said needle from said aperture of said biohazard receptacle while said holder is rotated to disengage said needle from said holder and for urging the disengaged needle into said interior of said biohazard receptacle.

7. The system of claim 6 wherein said means for preventing rotation of said needle is comprised of a post disposed within said aperture for engaging said ribbed segment of said needle hub.

8. The system of claim 6, wherein said locking means comprises a leaf spring having a tip for engaging said posterior surface of said horizontal band of said needle hub.

9. The system of claim 6, wherein said biohazard receptacle further comprises a semi-cylindrical skirt within said aperture having a leaf spring formed as an inwardly directed lip on said semi-cylindrical skirt for engaging said posterior surface of said needle hub.

10. A system for disposing of a double ended needle comprising:
- a double ended needle having an anterior end and a posterior end;
- a needle hub disposed on said double ended needle between said anterior end and said posterior end having:
  - (a) a posterior threaded segment;
  - (b) a segment having an enlarged diameter and a posterior surface; and
  - (c) an anterior ribbed segment;
- a blood collection holder having a boss for engaging said threaded segment of said needle hub; and
- a biohazard receptacle having:
  - (a) an interior for storing said needle following disengagement from said holder;
  - (b) an aperture for receiving the anterior end of said needle into said interior of said biohazard receptacle;
  - (c) means for engaging said ribbed segment of said needle hub in said aperture for preventing rotation of said needle as said holder is rotated, thereby disengaging said needle from said holder; and
  - (d) a leaf spring having a base fixed relative to said biohazard receptacle and a tip that is moved by insertion of said needle hub into said aperture into locking engagement with said posterior surface of said enlarged segment of said hub to prevent withdrawal of said needle from said aperture of said biohazard receptacle.

11. The system of claim 10 wherein said means for preventing rotation of said needle is comprised of a post disposed within said aperture for engaging said ribbed segment of said needle hub.

12. The system of claim 10, wherein said biohazard receptacle further comprises a semi-cylindrical skirt within said aperture, and said leaf spring is formed as an inwardly directed lip on said semi-cylindrical skirt for engaging said posterior surface of said needle hub.

13. A system for disposing of a needle comprising:
- a needle having a hub;
- a syringe having a boss for engaging said needle hub; and
- a biohazard receptacle having:
  - (a) an interior for storing said needle following disengagement from said holder;
  - (b) an aperture for receiving said needle into said interior of said biohazard receptacle;
  - (c) means for engaging said needle hub in said aperture for preventing rotation of said needle as said syringe is rotated, thereby disengaging said needle from said syringe; and
  - (d) locking means having a base fixed relative to said biohazard receptacle and a tip portion that is moved by insertion of said needle hub into said aperture into locking engagement with said hub to prevent withdrawal of said needle from said aperture of said biohazard receptacle while said syringe is rotated to disengage said needle from said syringe and for urging said disengaged needle into said interior of said biohazard receptacle.

14. The system of claim 13, wherein said needle hub comprises a ribbed segment and said means for preventing rotation of said needle is comprised of a post disposed within said aperture for engaging said ribbed segment of said needle hub.

15. The system of claim 13, wherein said biohazard receptacle further comprises a semi-cylindrical skirt within said aperture, and said spring locking means comprises a leaf spring formed as an inwardly directed lip on said semi-cylindrical skirt for engaging said needle hub.

16. A system for disposing of a double ended needle comprising:
- a double ended needle having an anterior end and a posterior end;
- a needle hub disposed on said double ended needle between said anterior end and said posterior end having:
  - (a) a posterior threaded segment;

(b) a segment having an enlarged diameter and a posterior surface adjacent said threaded segment; and (c) an anterior ribbed segment;

a blood collection holder having a boss for engaging said threaded segment of said needle hub to a position abutting said posterior surface of the needle hub, said boss having a smaller diameter than the diameter of said enlarged segment of said needle hub; and a biohazard receptacle having:

(a) an interior for storing said needle following disengagement from said holder;

(b) an aperture for receiving the anterior end of said needle into said interior of said biohazard receptacle;

(c) means for engaging said ribbed segment of said needle hub in said aperture for preventing rotation of said needle as said holder is rotated, thereby disengaging said needle from said holder; and (d) a leaf spring having a base fixed relative to said biohazard receptacle and a tip that is moved by insertion of said needle hub into said aperture into locking engagement with said posterior surface of said enlarged segment of said hub adjacent to said boss to prevent withdrawal of said needle from said aperture of said biohazard receptacle, and for urging said disengaged needle into the interior of said biohazard receptacle.

17. The system of claim 16, wherein said means for preventing rotation of said needle is comprised of a post disposed within said aperture for engaging said ribbed segment of said needle hub.

18. The system of claim 16, wherein said biohazard receptacle further comprises a semi-cylindrical skirt within said aperture, and said leaf spring is formed as an inwardly directed lip on said semi-cylindrical skirt for engaging said posterior surface of said needle hub.

* * * * *